United States Patent [19]

Lee et al.

[11] Patent Number: 5,030,567

[45] Date of Patent: * Jul. 9, 1991

[54] **METHOD FOR PRODUCTION OF L-PHENYLALANINE BY RECOMBINANT *E. COLI* ATCC 67460**

[75] Inventors: Sae Bae Lee; Chan Hee Won; Chung Park; Bun Sam Lim, all of Seoul, Rep. of Korea

[73] Assignee: Miwon Co., Ltd., Seoul, Rep. of Korea

[*] Notice: The portion of the term of this patent subsequent to Apr. 16, 2008 has been disclaimed.

[21] Appl. No.: 120,148

[22] Filed: Nov. 13, 1987

[30] Foreign Application Priority Data

Mar. 26, 1987 [KR] Rep. of Korea .................... 87-2815

[51] Int. Cl.$^5$ ..................... C12P 13/22; C12N 15/52; C12N 1/21; C12N 15/70

[52] U.S. Cl. ................................... 435/108; 435/69.1; 435/71.2; 435/170; 435/172.1; 435/172.3; 435/252.33; 435/320.1; 435/849; 536/27; 935/6; 935/8; 935/9; 935/14; 935/22; 935/29; 935/33; 935/39; 935/43; 935/59; 935/60; 935/61; 935/66; 935/72; 935/73

[58] Field of Search .................. 435/108, 172.1, 172.3, 435/849, 69.1, 71.2, 170, 252.33, 320; 935/66, 73, 6, 8, 9, 14, 22, 29, 33, 39, 43, 59, 60, 61, 72; 536/27

[56] References Cited

U.S. PATENT DOCUMENTS 4,681,852 7/1987 Tribe et al. ..................... 435/108

OTHER PUBLICATIONS

Shimatake et al. Nature vol. 292 (1981) pp. 128–137.
Maniatis et al. Molecular Cloning 1982, pp. 406–402.

*Primary Examiner*—Richard A. Schwartz
*Assistant Examiner*—Richard C. Peet
*Attorney, Agent, or Firm*—Birch, Stewart, Kolasch & Birch

[57] ABSTRACT

An *E. Coli* which can produce phenylalanine and which has an optimum phenylalanine production capability at a temperature of 30° to 35° C., and a process for preparing L-phenylalanine by use of the novel *E. coli* MWPEC 12-45 (ATCC 67460).

7 Claims, 1 Drawing Sheet

FIG. 1

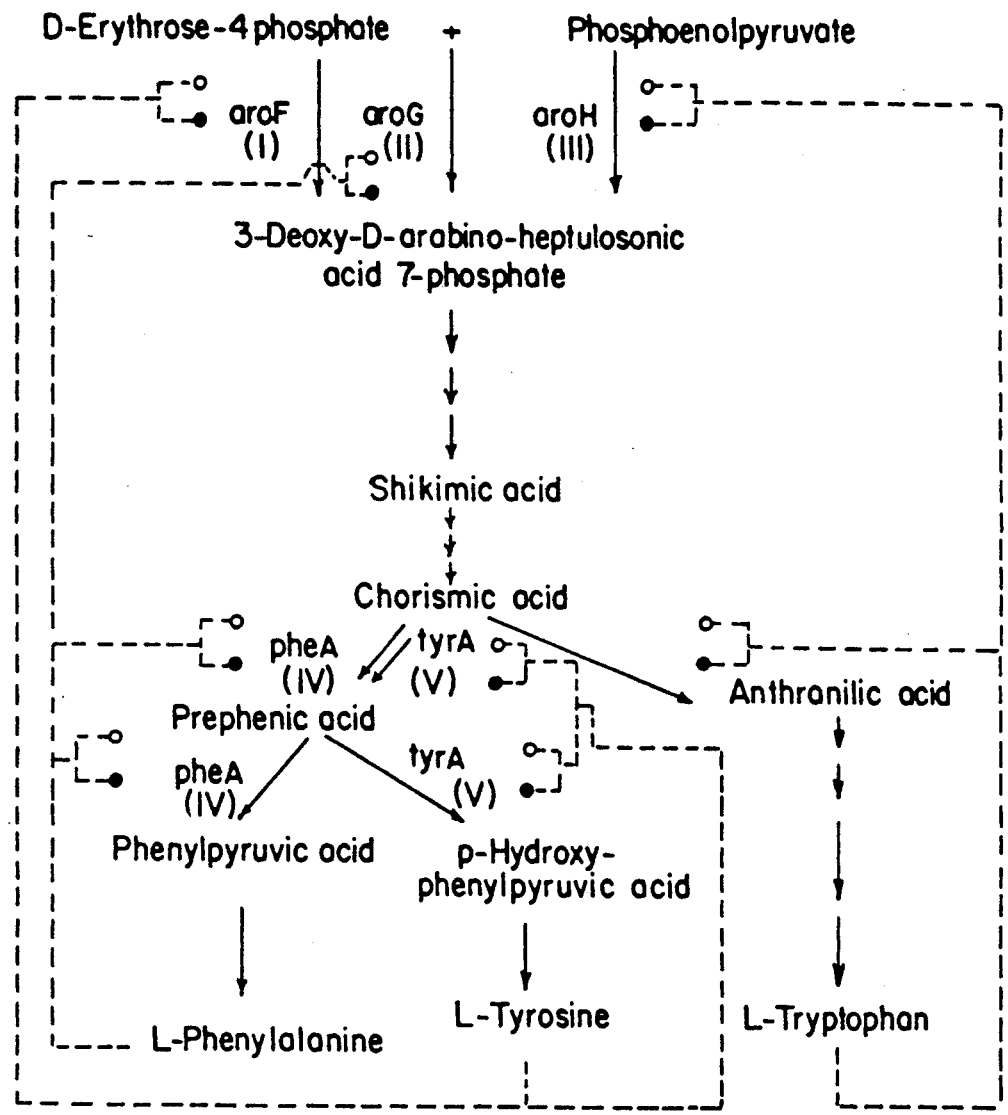

Wherein   I    is the DAHP synthase isoenzyme which is coded for by the aroF gene (tyrosine repressible)

II   is the DAHP synthase isoenzyme which is coded for by the aroG gene (phenylalanine repressible)

III  is the DAHP synthase isoenzyme which is coded for by the aroH gene (tryptophan repressible)

IV   is chorismate mutase P-prephenate dehydratase
V    is chorismate mutase P-prephenate dehydrogenase o    is feedback inhibition
•    is feedback repression

METHOD FOR PRODUCTION OF L-PHENYLALANINE BY RECOMBINANT *E. COLI* ATCC 67460

CROSS REFERENCE TO RELATED APPLICATION

This application is related to application Ser. No. 07/120,461 entitled "A Method For Production of L-Phenylalanine By Recombinant *E. coli*" filed concurrently herewith which is hereby incorporated by reference.

BACKGROUND OF THE INVENTION

1. Field of the Invention

The present invention relates to a method for production of L-phenylalanine by *Escherichia coli (E. coli)*. More particularly, the present invention relates to a novel *E. coli* containing a gene for the production of L-phenylalanine and a process for the production of L-phenylalanine by use of the novel microbe.

2. Description of the Prior Art

L-phenylalanine is a kind of essential amino acid and can be used for the synthetic production of ASPARTAME ®, a sweetening agent. There are many known methods for production of L-phenylalanine by use of microbes. For example, Japanese Kokai Nos. 37-6345 and 60-160,890 disclose methods for production of L-phenylalanine by use of Brevibacterium or Corynebacterium sp. which require tyrosine. Japanese Kokai 55-165,797 discloses a similar method by use of *E. coli* which requires tyrosine and which is resistant against tryptophan analogues. However, such prior art processes are not particularly suited for L-phenylalanine production on an industrial scale. Furthermore, these processes produce low yields of L-phenylalanine.

SUMMARY OF THE INVENTION

Accordingly, it is an object of the present invention to provide a novel *E. coli* which can produce phenylalanine and which has an optimum phenylalanine production capability at a temperature of 30° to 35° C., preferably 30° to 32° C. The *E. coli* may be transformed with a plasmid containing genes which produce enzymes in the pathway of L-phenylalanine biosynthesis. The plasmid may contain a temperature sensitive repressor whereby optimum expression of the plasmid is accomplished at 30°-35° C. as compared with more than 38° C. of the prior art. The plasmid may be the plasmid pMW11 containing a Kanamycin resistance gene, a pheA gene and a aroF gene. The restriction enzymes PstI, EcoRI and HindIII can be used to make the plasmid. The restriction enzymes AflII, HaeII, BamHI, may also be used to make the plasmid. A preferred *E. coli* of the present invention is MWPEC 12-45 (ATCC 67460) or a mutant thereof which possesses the same desirable phenylalanine production properties.

The present invention is also directed to a replicable recombinant plasmid which is capable of transforming an *E. coli* to produce a transformed *E. coli* having an optimum phenylalanine production capability at a temperature of 30°-35° C. The preferred plasmid is derived from *E. coli* MWPEC 12-45 (ATCC 67460). The plasmid preferably contains the pheA and aroF genes and a temperature sensitive promoter which controls the expression of said genes.

The present invention is also directed to a method for the production of phenylalanine which comprises cultivating the *E. coli* of the present invention in a culture medium. The cultivation is preferably carried out at a temperature of 30° to 35° C., more preferably 30° to 32° C. The culture medium will contain a primary food source such as sugar and other essential nutrients. The sugar may be glucose or a hydrolyzed mixture of glucose, fructose and sucrose. The method may also comprise the steps of aerating and agitating the culture media and recovering phenylalanine from the culture media. The phenylalanine may also be purified.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawing which is given by way of illustration only, and thus are not limitative of the present invention, and wherein:

FIG. 1 illustrates the metabolic pathways for biosynthesis of aromatic amino acids in a *E. coli*.

DETAILED DESCRIPTION OF THE INVENTION

Referring now in detail to the drawing for the purpose of illustrating the present invention, as shown in FIG. 1, the process for preparing L-phenylalanine by use of the recombinant plasmid is controlled by enzyme action in *E. coli* cells. One of the enzymes which controls the reaction is chorismate mutase p-prephenate dehydratase. One of the other enzymes which controls the reaction is the enzyme, 3-deoxy-D-arabinoheptulosonate-7-phosphate synthase (DAHP synthase). The DAHP synthase exists as three isoenzymes which are coded for by the aroF, aroG and aroH genes, respectively.

According to the present invention, the aroF and pheA genes for use in L-phenylalanine production are derived from a *E. coli* MWEC 101-5 (KAIST, KCTC 8234p) by a shot gun method. At this time, the *E. coli* MWEC 101-5 is released from the control of the living synthetic metabolism.

Accordingly, the genetically engineered strain MWPEC 12-45 (ATCC 67460, July 14, 1987: KAIST, KCTC 8236P, Mar. 25, 1987) of the present invention can be used in the process for production of L-phenylalanine at certain temperatures without any adverse influence on the production of L-phenylalanine.

The general method for preparing the plasmid is described in Recombinant DNA Methodology (Jo-Anne R. Dillion, Anwar Nasim, Earle R. Nestmann) and Molecular Cloning (T. Maniatis, E. F. Fritsch, J. Sambrook).

The novel microbe, *E. coli* MWPEC 12-45, according to the present invention can be prepared as follows:

After MWEC 101-5 strain is cultivated and agitated in LB culture media (1% of bactotryptone, 0.5% of bactoyeast extract, 1% of sodium chloride, pH 7.4) at 37° C. for 15 hours, the cells are harvested. The chromosomal DNA (cDNA) was isolated by CsCl density gradient centrifugation method. Thereafter, the cDNA was purified by butanol treatment and dialysis.

Plasmids from E. coli HB101/pBR322, E. coli pPLC 2833 and E. coli HB101/pMK20 to be utilized in the present invention are also isolated and purified by the above-mentioned process steps. The cDNA is digested with EcoRI completely in medium salt restriction enzyme buffer (50 mM of sodium chloride, 10 mM of tris (pH 7.5), 10 mM of magnesium chloride, and 1 mM dithiothreitol) at 37° C. for 1 hour. The restriction enzyme is inactivated in a conventional manner and the cDNA is further digested with the restriction enzyme PstI. A 4–7 kb fragment is recovered in 0.7% by weight of Agarose gel to be a target gene. The plasmid pBR322 is digested with the above-mentioned restriction enzymes, PstI and EcoRI. The digested plasmid pBR322 is mixed with the 4–7 kb gene fragment produced from E. coli MWEC 101-5 in an amount of 1:3. The digested plasmid and gene fragment are combined with each other in T4DNA ligase buffer solution (0.5 M of tris (pH 7.4), 0.1 M of magnesium chloride, 0.1 M of dithiothreitol, 10 mM of spermidine, 10 mM of ATP, 1 mg/ml of bovine serum albumin) at 12° C.–14° C. for 12 hours.

The ligation mixture containing the combined recombinant plasmid is used to transform the phenylalanine auxotroph (pheA-deficiency strain) MWEC 203-7 by the calcium chloride method of Nogard. The transformant is maintained in MM culture media (10 g of glucose, 4 g of ammonium sulfate, 2 g of potassium phosphate, 0.5 g of magnesium sulfate, 20 mg of ferrous chloride, 10 mg of manganese chloride, 1 mg of thiamine hydrochloride salt, 0.5 g of fumaric acid, 1 l of distilled water, pH 7.4) at 37° C. for 1 hour. The treated strain is plated onto an agar MM culture media containing 15 μg/ml of tetracycline and cultivated for 10 days. The recombinant strain which grows on MM is selected. The plasmid pMW10 is isolated from the selected strain and digested with the restriction enzyme, HindIII, partially digested again with the restriction enzyme PstI, and the restriction enzymes are inactivated. A desired fragment containing the pheA and aroF genes is separated from 0.7% agarose gel.

T4 DNA polymerase and dNTP mixture solution (25 mM of dATP, 25 mM of dGTP, 25 mM of dCTP and 25 mM of dTTP) are added to the plasmid to convert the sticky ends to blunt ends.

Plasmid pMK20 containing a Kanamycin antibiotic resitance gene (Km) is treated with PstI and is added to the T4DNA polymerase and DNTP mixture solution to convert its sticky ends to blunt ends.

The pheA deficient strain, MWEC 203-7 is transformed according to the same method as mentioned above. The recombinant plasmid pMW11 is separated from cultivated strains which grew on MM agar media containing 50 μg/ml kanamycin.

The plasmid pPLc 2833 which contains the $p_L$ promoter was treated with the restriction enzyme BamHI, HaeII and a 0.2 kb $P_L$ fragment was recovered on 2% agarose gel.

The fragment was treated with T4 DNA polymerase and dNTP to form a blunt end at both ends.

The recombinant plasmid pMW11 was digested with AflII and treated by the same method as the above-mentioned to form a blunt end at both ends.

The $P_L$ fragment was added to the treated pMW11 and ligated to produce a recombinant plasmid. The recombinant plasmid is used to transform the MWEC 203-7 strain.

A pMW12 recombinant plasmid is separated from the transformed recombinant strain. The pMW12 recombinant plasmid is larger than pMW 11 plasmid by 0.2 kb.

The product was treated by fragment T4 DNA polymerase and dNTP to form a blunt end at both ends, after being digested with DdeI.

The plasmid pPLc2833 was digested with BamHI and HaeII to obtain the $P_L$ fragment thereof and blunt ends were formed on the $P_L$ fragment.

The $P_L$ fragment was added to the treated pMW 12 to produce a recombinant plasmid which was used to transform the MWEC 203-7 strain.

A pMW12-1 recombinant plasmid was separated from the transformed recombinant strain. The pMW12-1 recombinant plasmid is larger than pMW11 plasmid by 0.4 kb.

The E. coli MWEC 101-5 (KAIST, KCTC 8234P) is transformed with the pMW12-1 to produce a novel strain MWPEC 12-45 for use in manufacturing the L-phenylalanine. The novel strain MWPEC 12-45 was deposited at the American Type Culture Collection on July 14, 1987 in accordance with the conditions of the Budapest Treaty and was assigned deposit number ATCC 67460.

The biochemical properties of the novel strain MWPEC 12-45 (ATCC 67460) are the same as those of host strain MWEC 101-5. However, the yield of L-phenylalanine of the novel strain MWPEC 12-45 (ATCC 67460) is increased when compared with the parent strain as follows (Table I):

TABLE I

| Strain | Yield of L-phenylalanine | |
|---|---|---|
| | Plasmid | Yield of L-phenyl-alanine (g/l) |
| MWEC 101-5 | None | 7.9 |
| MWPEC 10-15 | pMW10 | 19.6 |
| MWPEC 11-30 | pMW11 | 24.3 |
| MWPEC 12-45 | pMW12-1 | 28.7 |

The above data was obtained by following the procedures reported in Example 1.

EXAMPLE 1

(A) Strain

MWPEC 12-45

(B) Seed Medium

| Glucose | 5% |
|---|---|
| Bactotryptone | 1% |
| Bactoyeast extract | 1% |
| Sodium chloride | 0.1% |
| kanamycin | 10 mg/l |
| pH | 7.0 |

(C) Fermentation Media

| Glucose | 6% | Glutamic acid | 0.05% |
|---|---|---|---|
| Calcium sulfate | 0.04% | Cobaltous chloride | 0.1 mg/l |
| Ammonium sulfate | 2% | Zinc sulfate | 1 mg/l |
| Sodium citrate | 0.05% | Manganous chloride | 2 mg/l |
| Fumaric acid | 0.05% | Calcium chloride | 5 mg/l |
| Magnesium chloride | 0.08% | Thiamine Hydro-chloride salt | 10 mg/l |
| Potassium phosphate, monobasic | 0.1% | Nicotinic Acid | 10 mg/l |
| Potassium phosphate, dibasic | 0.1% | pH | 7.0 |

| | |
|---|---|
| -continued | |
| Bactoyeast extract | 0.1% |

(D) Fermentation Method 50 ml of the seed medium is charged into 500 ml of a test flask and heated at 120° C. for 20 minutes. The novel *E. coli* strain MWPEC 12-45 (ATCC 67460) is added to the flask and cultivated under 120 rpm at 30° C. for 24 hours. The fermentation media is prepared by the above-mentioned method.

20 l of the fermentation media is charged into 50 l of fermenter, heated and sterilized at 120° C. for 20 minutes. 1 l of the culture media is charged into the fermentation media under 400 rpm and 0.75 vvm (oxygen rate) at 32° C. for 50-60 hours.

During fermentation, the pH is maintained at 7.0 by adding ammonium hydroxide and a 60% glucose solution to the fermentation apparatus two times when the level of glucose falls below 1%.

The total mol amount of glucose which is used in the fermentation is 140 g/l. L-phenylalanine is obtained at a concentration of 28.7 g/l. 1 l of fermentation solution is purified by a conventional method such as absorbing with ion-exchange resin and isolating with ammonium hydroxide to produce 25.3 g of L-phenylalanine as crude crystals.

EXAMPLE 2

Example 1 was repeated except that the glucose was replaced by a mixture of the sugars fructose, glucose and sucrose which has been hydrolyzed by invertase in the Example 2. The concentration of L-phenylalanine produced was 29.3 g/l.

What is claimed is:

1. An *E. coli* which can produce phenylalanine and which has an optimum phenylalanine production capability at a temperature of 30° to 32° C. which is ATCC 67460.

2. A process for production of phenylalanine which comprises cultivating an *E. coli* strain which has the plasmid from ATCC 67460.

3. The process of claim 2, wherein the *E. coli* is cultivated at a temperature of 30° to 35° C.

4. The process of claim 3, wherein the temperature is 30° to 32° C.

5. The process of claim 2, wherein cultivation is conducted in the presence of sugar.

6. The process of claim 5, wherein the sugar is a hydrolyzed mixture of glucose, fructose and sucrose.

7. A replicable recombinant plasmid isolated from ATCC 67460 which is pMN12-1 and is capable of transforming an *E. coli* to produce phenylalanine.

* * * * *